United States Patent
Baugh

(12) 
(10) Patent No.: US 6,468,287 B1
(45) Date of Patent: *Oct. 22, 2002

(54) LANCET FOR CAPILLARY PUNCTURE BLOOD SAMPLES

(75) Inventor: Robert F. Baugh, Parker, CO (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/308,414
(22) PCT Filed: Apr. 30, 1997
(86) PCT No.: PCT/US97/08574
§ 371 (c)(1), (2), (4) Date: Oct. 29, 1998
(87) PCT Pub. No.: WO97/42873
PCT Pub. Date: Nov. 20, 1997

Related U.S. Application Data

(63) Continuation-in-part of application No. 08/640,276, filed on Apr. 30, 1996, now Pat. No. 5,674,236.
(51) Int. Cl.[7] .................................................. A61B 5/00
(52) U.S. Cl. ...................... 606/181; 600/583; 600/576; 606/266
(58) Field of Search ................................ 606/181–183; 604/266; 600/583, 576

(56) References Cited

U.S. PATENT DOCUMENTS

| 4,624,256 A | * | 11/1986 | Messier et al. ............. 606/230 |
| 4,967,763 A | * | 11/1990 | Nugent et al. |
| 5,014,718 A |   | 5/1991  | Mitchen |
| 5,029,583 A |   | 7/1991  | Meserol et al. |
| 5,167,960 A |   | 12/1992 | Ito et al. |
| 5,182,317 A |   | 1/1993  | Winters et al. |
| 5,275,953 A | * | 1/1994  | Bull |
| 5,492,763 A |   | 2/1996  | Barry et al. |
| 5,525,348 A | * | 6/1996  | Whitbourne et al. |
| 5,552,323 A | * | 9/1996  | Mercereau ................... 600/583 |
| 6,110,483 A | * | 8/2000  | Whitbourne et al. |

FOREIGN PATENT DOCUMENTS

| DE | 0 440 961 | 8/1991 |
| GB | 2232599   | 12/1990 |

* cited by examiner

Primary Examiner—George Manuel
Assistant Examiner—Runa Shoh Qaderi
(74) Attorney, Agent, or Firm—Steven C. Petersen; Sarah S. O'Rourke; Hogan & Hartson LLP

(57) ABSTRACT

A piercing instrument (12) for obtaining a non-activated drop of blood (B) by capillary puncture is formed by depositing a coating agent (20) on the exterior surface of the piercing instrument (12). The coating agent comprises compounds that inhibit the activation of blood.

30 Claims, 1 Drawing Sheet

LANCET FOR CAPILLARY PUNCTURE BLOOD SAMPLES

The present invention is a Section 371 filing of PCT/US97/08574, filed Apr. 30, 1997, which is a Continuation-in-Part of U.S. patent application Ser. No. 08/640,276, filed Apr. 30, 1996, now issued as U.S. Pat. No. 5,674,236.

DESCRIPTION

1. Technical Field

The present invention relates generally to an apparatus and method for obtaining blood samples useful in diagnostic testing, and more particularly, to an apparatus and method for obtaining a non-activated capillary puncture blood sample for blood coagulation assays.

2. Background Art

Blood coagulation is a complex chemical and physical reaction which occurs when blood comes into contact with an activating agent, such as an activating surface or an activating reagent. In accordance with one simplified conceptual view, the whole blood coagulation process can be generally viewed as three activities: agglutination of platelets, blood clotting, and fibrous tissue formation. In vivo, platelets flow through the blood vessels in an inactivated state because the blood vessel lining, the endothelium, prevents activation of platelets. When a blood vessel is damaged, however, the endothelium loses its inert character and platelets are activated by contact with tissue underlying the damaged site. Activation of the platelets causes them to become "sticky" and adhere together. Additional platelets then adhere to the activated platelets and also become activated. This process continues until a platelet "plug" is formed. This platelet plug then serves as a matrix upon which blood clotting proceeds.

If the chemical balance of the blood is suitable, thrombin is then produced which causes conversion of fibrinogen to fibrin, which forms the major portion of the clot mass. During clotting, additional platelets are activated and trapped in the forming clot, contributing to clot formation. As clotting proceeds, polymerization and cross-linking of fibrin serves as the permanent clot. Thus, platelet activation plays a very important function in blood coagulation. This particular mode of blood coagulation is termed the "intrinsic" coagulation pathway.

Blood and plasma also contain a family of serine proteases that regulate the intrinsic clotting process but also regulate the extrinsic coagulation pathway through bypassing a number of early time-consuming steps in the intrinsic coagulation pathway discussed previously. These serine proteases are referred to as coagulation "factors", are typically designated with Roman Numerals (with an "a" suffix added. if the factor is in an enzymatically active state), and operate in a precisely regulated amplification cascade to form blood clots at the site where tissue has been injured. These blood clots act to stop bleeding at the site of injury. This particular mode of blood coagulation is termed the "extrinsic" coagulation pathway.

Normal tissue contains a membrane bound glycoprotein, called tissue factor, which is liberated when the tissue is injured. The extrinsic coagulation process begins when this tissue factor forms a complex with coagulation factor VII and/or VII(a). This tissue factor factor VII(a) complex in turn activates factor X, which in concert with co-factor V, transforms the inactive prothrombin protease into the active thrombin enzyme. Thrombin then transforms fibrinogen into fibrin, which forms the actual blood clot.

Blood coagulation tests may be performed for a variety of purposes, including determination of the bleeding susceptibility of patients undergoing surgery and monitoring of patients undergoing anti-coagulation therapy for the prevention of blood clots. A variety of coagulation tests are presently in use. One of the most popular is the "prothrombin time" (PT) test which relies on induction of the extrinsic coagulation pathway by activation of coagulation protease factor VII by thromboplastin in a blood sample to be tested.

There have been a variety of devices developed for collecting blood samples. For example, Summers discloses a two-chamber syringe which separates blood cells from plasma. The first chamber is filled with a filtering material which may incorporate anticoagulants. Blood being drawn into the syringe is filtered through this first chamber allowing only the cell-free component of the blood to enter and be collected in the second chamber. See patent No. GB 2,232, 599. A second technique for collecting a blood sample is disclosed by Mitchen in his U.S. Pat. No. 5,014,718. The Mitchen reference discloses an apparatus for piercing a patients skin and collecting the resultant blood sample in a liquid vehicle which is adsorbed on to a porous test disk. Mitchen further teaches the addition of an anticoagulant to the liquid vehicle to avoid coagulation and hemolysis.

The above patents by Summers and Mitchen each disclose methods for collecting blood samples. The aim of the Summers patent, however, is to carry out the separation of blood cells from plasma or serum and to thus collect the serum, while Mitchen's goal is to more efficiently transport blood to a filter paper by increasing the total liquid volume present.

While capillary puncture blood samples may be obtained by puncturing the skin with a lancet or needle, the trauma of such needle injection typically releases tissue juices and the like into the emerging blood thereby modifying the blood coagulation characteristics. Consequently, to achieve optimal test results, freshly drawn venous blood is typically utilized in the PT test. Thus, the PT test is generally limited to clinical laboratories. Although such centralized testing may be adequate for surgical patients, visiting a doctor's office or a clinic on a regular basis to monitor anti-coagulation therapy is less acceptable. Thus the need for a convenient, practical, and reliable means of obtaining non-activated capillary puncture blood samples at a patient's home is needed.

DISCLOSURE OF INVENTION

Accordingly, it is an object of the present invention to provide a method for obtaining a non-activated capillary puncture blood sample.

A further object of the present invention is to reduce the trauma resulting from tissue puncture by a medical device, such as, a lancet or needle.

Additional objects, advantages, and novel features of the invention shall be set forth in part in the description that follows, and in part will become apparent to those skilled in the art upon examination of the following or may be learned by the practice of the invention. The objects and the advantages may be realized and attained by means of the instrumentalities and in combinations particularly pointed out in the appended claims.

To achieve the foregoing and other objects and in accordance with the purposes of the present invention, as embodied and broadly described herein, the apparatus of this invention may comprise a piercing instrument for obtaining a non-activated capillary puncture blood sample wherein a composition that inhibits contact activation of blood emerging from damaged tissue is removably disposed on the piercing instrument.

To further achieve the foregoing and other objects and in accordance with the purposes of the present invention, as embodied and broadly described herein, the method of this invention may comprise the steps of coating a surface of a piercing instrument with a removable composition that inhibits contact activation of blood emerging from damaged tissue; and puncturing a bodily tissue with said piercing instrument thereby dislodging said removable composition in the puncture.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

BEST MODE FOR CARRYING OUT THE INVENTION

Figure 1:
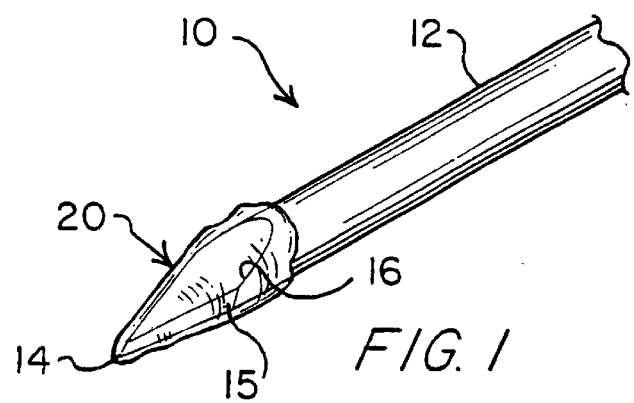
FIG. 1 is a perspective view of a treated piercing instrument of the present invention.

In general, the present invention relates to medical devices and a method for obtaining a non-activated capillary puncture blood sample for coagulation assays. The medical device 10 according to the present invention shown in FIGS. 1 and 2, includes a removable composition or coating agent 20 disposed on a surface of a piercing instrument 12 designed to come into contact with and puncture bodily tissues. Essentially, as medical device 10 punctures the bodily tissue the removable coating agent 20 adheres to the damaged tissue 19 creating an artificial barrier 20' between the damaged tissue 19 and the blood B emerging from the puncture site 18. Barrier 20' does not function as a barrier in the sense of an impenetrable layer which isolates the emerging blood B from the damaged tissue 19; instead, the compounds comprising barrier 20' inhibit or block the activation of events occurring in the damaged tissue from coming in contact with and activating the emerging blood. This gives rise to a drop of non-activated blood (not shown) which is suitable for diagnostic coagulation tests. While the detailed discussion below refers to human bodily tissues, it is also contemplated and to be understood that the medical device 10 of the present invention would also function on non-human bodily tissues encountered in the field of veterinarian medicine.

Figure 2:
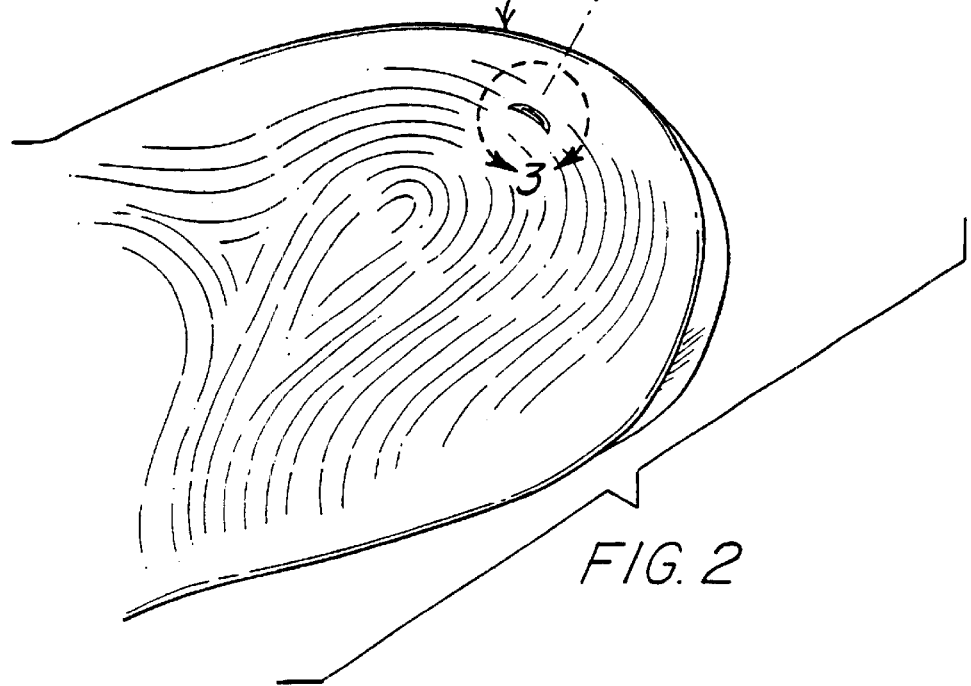
FIG. 2 is a perspective view of a bodily tissue puncture resulting from the treated blood lancet of the present invention.

More specifically, medical device 10 in the preferred embodiment of the present. invention shown in FIGS. 1 and 2, includes a removable coating agent 20 disposed on the exterior surface 15 of piercing instrument 12. Piercing instrument 12 may be formed from metallic, ceramic, and/or polymeric materials, or a combination of such materials, and requires a pointed end 14 that comes in contact with and is capable of puncturing bodily tissues, such as, the tip of a human finger F. Preferably, piercing instrument 12 is a stainless steel lancet having a beveled surface 16; however, needles having a conical end, tubular needles, such as hypodermic needles, and capillaries may also be used.

The microanatomy of a finger prick puncture for obtaining a non-activated blood sample requires the inhibition of at least one of the following four activation mechanisms (i) contact activation of the intrinsic coagulation system; (ii) fibrinolysis activation by contact activation; (iii) platelet activation by connective tissue; and (iv) tissue factor activation of extrinsic coagulation. Consequently, removable coating agent 20 preferably comprises one or more compounds that inhibit at least one of the four previously discussed activation mechanisms.

The first two mechanisms, that is, contact activation of the intrinsic coagulation system and fibrinolysis activation by contact activation, may be blocked by serine protease inhibitors or analogs thereof. Aprotinin, which is presently isolated from bovine lungs, is commonly used to reduce post-surgical blood loss in bypass surgery and is the preferred serine protease inhibitor; however, analogs of aprotinin and other serine protease inhibitors may also be used. Moreover, any substance which is known or found to be functionally equivalent to serine protease inhibitors in inhibiting contact activation of the intrinsic coagulation system and fibrinolysis activation by contact activation may be used to practice the present invention.

The third mechanism, that is, platelet activation by connective tissue may be prevented by using any of several different antiplatelet compounds. The following list is meant to exemplify the various antiplatelet compounds available and is not meant to be limiting. Antiplatelet compounds that are embodied within the present invention include but are not limited to prostacylin, IIb/IIIa inhibitor sold under the trademark ReoPro (also referred to as "Abciximab," which is the Fab fragment of the chimeric human-murine monoclonal antibody 7E3, RGD peptide, or similar analogs. ReoPro was obtained from iCentocor BV (Leiden, The Netherlands). Although these are the presently preferred inhibitors of platelet activation by connective tissue, any substance which is known or subsequently found to be functionally equivalent to the preferred inhibitors may be used in the practice of the present invention. Although the concentration of this inhibitor required to achieve the desired effect will depend upon the efficiency of inhibition of the particular agent.

The fourth and last mechanism, that is, tissue factor (thromboplastin) inhibition may be accomplished using an inhibitory substances, such as an antibody, for example a monoclonal antibody or its equivalent, to thromboplastin. The production of antibodies is well-known to those skilled in. the art of molecular biology and standard methods are disclosed by T. Maniatis et al., Molecular Cloning: A Laboratory Manual. Cold Spring Harbor Laboratory, Cold Spring Harbor, N.Y., and S. Berger et al., Guide to Molecular Cloning Techniques, Academic Press, Inc. 1987. Again, the concentration of the tissue factor inhibitor required to achieve the desired result will depend upon the particular inhibitory agent.

Figure 3:
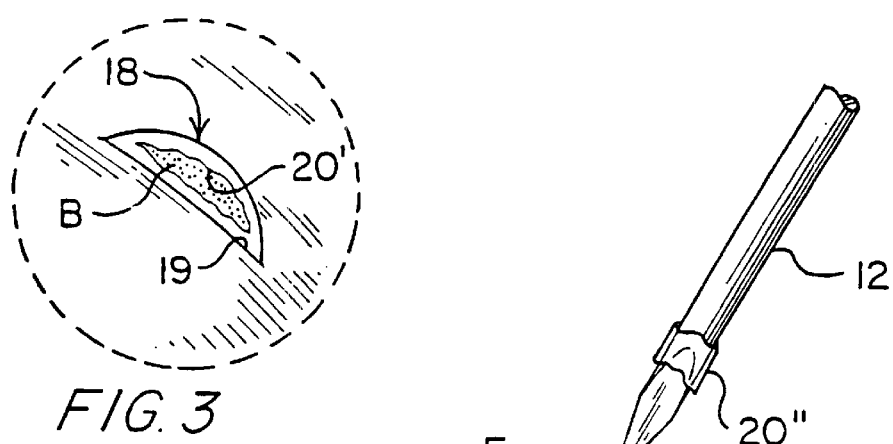
FIG. 3 is a magnified view of the bodily tissue puncture shown in FIG. 2 resulting from the treated piercing instrument of the present invention. Replacement

In practice, medical device 10 of the present invention is prepared by depositing a suspension comprising a serine protease inhibitor, an antiplatelet inhibitor and an antibody to thromboplastin over the exterior surface 15 of the pointed end 14 of piercing instrument 12 utilizing microscopic spraying or deposition processes, such as, but not limited: 1.) dip coating; 2) chemical vapor deposition; and 3.) spraying. The deposited suspension dries over the exterior surface 15 thereby providing a removable coating agent 20. As shown in FIGS. 2 and 3 rapidly striking bodily tissue F with medical device 10 of the present invention results in a puncture 18 being formed wherein removable coating agent 20 is dislodged from piercing instrument 12 and adheres to the damaged tissue 19 forming a barrier 20' between the damaged tissue 19 and the emerging blood B.

In a second embodiment, the removable coating agent 20 further comprises a bacteriostatic/bactericidal agent, such as, but not limited to: penicillin G, methicillin, gentamicin, erythromycin, isoniazid, amphicillin, cephalospqrins, streptomycin, kanamycin, tetracyclines, chloramphenicols, sulfonamides, and neomycin. The presence of the bacteriostatic/bactericidal agent has a two-fold advantage. First, in preparing the medical device 10 of the present invention, in an aseptic environment, the bacteriostatic/bactericidal agent may function to sterilize medical device 10 and second it may fight off infection at the puncture site. However, the bacteriostatic/bactericidal agent ultimately used must not interfere or alter coagulation.

In a third embodiment, of the present invention an analgesic compound, such as, but not limited to: lidocaine and benzocaine, may be added to the removable coating agent 20 disclosed in the preferred and second embodiments.

In a fourth embodiment, of the present invention (not shown) the removable coating agent 20 may be disposed on the interior surface of a tubular needle or capillary.

The foregoing description is considered as illustrative only of the principles of the invention. Furthermore. since a number modifications and changes will readily occur to those skilled in the art, it is not desired to limit the invention to the exact construction and process shown described above. Accordingly, all suitable modifications and equivalents may be resorted to falling within the scope of the invention as defined by the claims which follow.

What is claimed is:

1. A lancet for obtaining a drop of blood for analysis by capillary puncture comprising a needle having an exterior surface that is adapted to puncture skin and a removable coating on said exterior surface wherein the portion of said coating that comes in contact with a puncture site obtained by capillary puncture with said needle is transferred from said needle to said puncture site, said coating comprising a composition which inhibits contact activation of the drop of blood at said puncture site.

2. A lancet as defined in claim 1, wherein said coating further comprises a material that is capable of inhibiting fibrinolysis.

3. A lancet as defined in claim 1, wherein said coating further includes a material that is capable of inhibiting platelet activation of said drop of blood.

4. An apparatus for obtaining blood samples by capillary puncture comprising a lancet and a removable coating on the surface of said lancet wherein the portion of said coating that comes in contact with a puncture site obtained by capillary puncture with said lancet is transferred from said lancet to said puncture site, said coating including a blood platelet inhibitor, a serine protease inhibitor, and a monoclonal antibody to thromboplastin.

5. An apparatus as defined in claim 4, wherein said serine protease inhibitor is aprotinin.

6. An apparatus as defined in claim 4, wherein said composition further comprises a bacteriostatic or bactericidal agent.

7. An apparatus as defined in claim 4, wherein said composition further comprises an analgesic compound.

8. An apparatus for inhibiting contact activation of blood, comprising an instrument adapted to puncture a bodily tissue and having an exterior surface coated with a removable composition, wherein the portion of said coating that comes in contact with a puncture site obtained by capillary puncture with said instrument is transferred from said instrument to said puncture site, said composition comprising one or more compounds that specifically inhibit one or more blood activation mechanisms at the puncture site.

9. The apparatus of claim 8, wherein one or more of said compounds specifically inhibits one or more blood activation mechanism.

10. The apparatus of claim 9, wherein said composition comprises a blood platelet inhibitor, a serine protease inhibitor, and an antibody to thromboplastin.

11. The apparatus of claim 10, wherein said composition further comprises an analgesic.

12. The apparatus of claim 10, wherein said composition further comprises a bacteriostatic or bactericidal agent.

13. The apparatus of claim 8, wherein said composition comprises a compound that inhibits contact activation of the intrinsic coagulation system.

14. The apparatus of claim 8, wherein said composition comprises a compound that inhibits fibrinolysis activation by contact activation.

15. The apparatus of claim 8, wherein said composition comprises a compound that inhibits platelet activation by connective tissue.

16. The apparatus of claim 8, wherein said composition comprises a compound that inhibits tissue factor activation of extrinsic coagulation.

17. A method of obtaining a drop of blood for analysis, comprising the steps of:
coating an outside surface of a lancet with a removable composition that inhibits contact activation of the drop of blood; and
puncturing a bodily tissue with said outside surface of said lancet to obtain the drop of blood, wherein the portion of said composition that comes in contact with said bodily tissue is transferred from said lancet to said puncture site.

18. The method of claim 17, wherein said composition includes a compound that inhibits fibrinolysis activation by contact activation.

19. The method of claim 18, wherein said composition includes a serine protease inhibitor.

20. The method of claim 17, wherein said composition includes a compound that inhibits platelet activation by connective tissue.

21. The method of claim 20, wherein said compound is a prostacylin analog.

22. The method of claim 17, wherein said composition includes a compound that inhibits tissue factor activation of extrinsic coagulation.

23. The method of claim 17, wherein said composition inclides a compound that inhibits contact activation of the intrinsic coagulation system.

24. The method of claim 17, wherein said composition prevents contact activation of the drop of blood at the site of the punctures bodily tissue.

25. A method for obtaining a non-activated drop of blood comprising:
coating a surface of an instrument with a removable composition comprising a serine protease inhibitor, a blood platelet inhibitor, and a monoclonal antibody to thromboplastin; and
puncturing a bodily tissue with said instrument, thereby transferring the portion of said composition that comes in contact with the puncture site from said instrument to the puncture site wherein said serine protease inhibitor, said blood platelet inhibitor, and said monoclonal antibody inhibit one or more blood activation mechanisms.

26. An improved lancet for obtaining a drop of blood for analysis by capillary puncture of a bodily tissue, wherein the improvement comprises said lancet having a removable coating thereon of a composition which precludes contact activation, platelet activation, and fibrinolysis of the blood sample, wherein the portion of said coating that comes in contact with a bodily tissue is transferred from said lancet to the puncture site.

27. An improved lancet as defined in claim 26, wherein said composition includes a serine protease inhibitor or analogues thereof.

28. An improved lancet as defined in claim 27, wherein said serine protease inhibitor is aprotinin.

29. An improved lancet as defined in claim 26, wherein said composition includes an antiplatelet compound.

30. An improved lancet as defined in claim 29, wherein said antiplatelet compound is prostacyclin.

* * * * *